United States Patent [19]

Stallings

[11] Patent Number: 4,459,707
[45] Date of Patent: Jul. 17, 1984

[54] EAR PROTECTING DEVICE
[75] Inventor: John P. Stallings, Indianapolis, Ind.
[73] Assignee: Cabot Corporation, Kokomo, Ind.
[21] Appl. No.: 410,726
[22] Filed: Aug. 23, 1982
[51] Int. Cl.$^3$ ............................................. A42B 1/06
[52] U.S. Cl. ........................................ 2/209; 2/208; 181/20; 181/256
[58] Field of Search ...................... 2/208, 209; 181/20, 181/256

[56] References Cited

U.S. PATENT DOCUMENTS

| | | |
|---|---|---|
| 1,909,856 | 5/1933 | Dolder . |
| 2,782,423 | 1/1954 | Simon et al. ............................ 2/209 |
| 2,901,751 | 9/1959 | Gales et al. ............................. 2/209 |
| 3,112,005 | 7/1960 | Shaw et al. ............................. 2/209 |
| 3,454,962 | 7/1969 | Hind ........................................ 2/209 |
| 3,588,914 | 6/1971 | Ihnat, Jr. . |
| 3,637,040 | 1/1972 | Gorman .................................. 2/209 |
| 3,644,939 | 2/1972 | Beguin . |
| 3,661,225 | 5/1972 | Anderson . |
| 3,728,741 | 4/1973 | Lepor ...................................... 2/209 |
| 3,823,713 | 7/1974 | Shah ....................................... 2/209 |
| 3,943,572 | 3/1976 | Aileo ...................................... 2/209 |
| 4,094,303 | 6/1978 | Johnston ............................. 494/303 |
| 4,174,155 | 11/1979 | Herman . |

OTHER PUBLICATIONS

Journal of the Acoustical Society of America, vol. 15, No. 3, pp. 158 & 159, Jan. 1944.
Journal of the Acoustical Society of America, vol. 27, pp. 146 & 147, Jan. 1955.

Primary Examiner—Werner H. Schroeder
Assistant Examiner—Mary A. Ellis
Attorney, Agent, or Firm—Jack Schumna; Robert F. Dropkin

[57] ABSTRACT

An ear protecting device for protecting a wearer from annoying and/or damaging noise levels. The device is comprised of a connecting member and a pair of muffs suitable for covering a wearer's ears. The muffs are suspended from opposite portions of the connecting member. The muffs are permeable to water vapor. Each said muff is at least partially porous. Each said muff has a specific airflow resistance of at least 15,000 SI rayls. Each said muff has a permeance of at least 2 metric perms.

22 Claims, 5 Drawing Figures

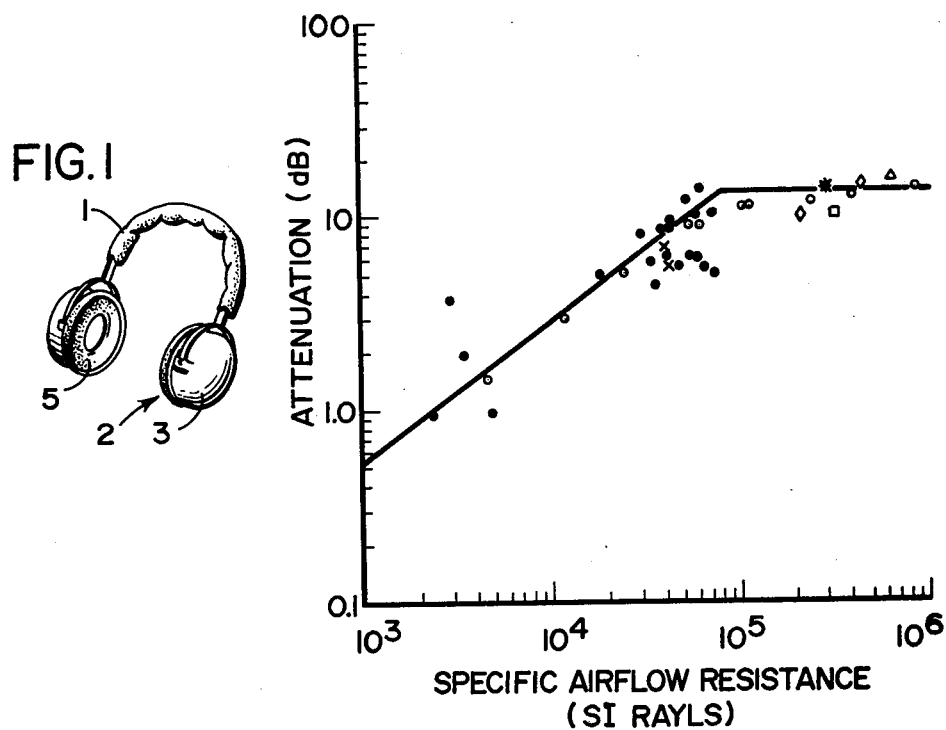
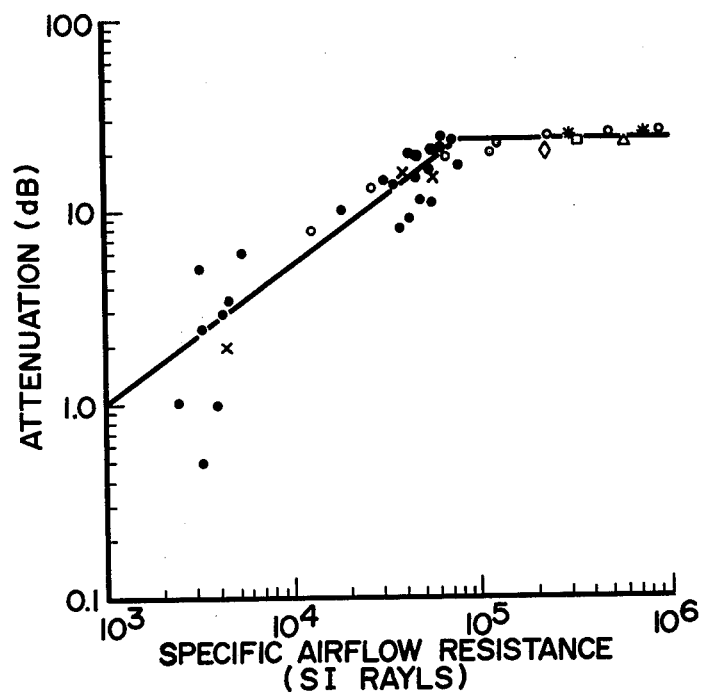

EAR PROTECTING DEVICE

The present invention relates to an ear protecting device.

Numerous ear protecting devices have been developed for protecting a wearer from annoying and/or damaging noise levels. One class of such devices, generally known as earmuffs, is comprised of a connecting member and a pair of muffs suitable for covering a wearer's ears. The muffs are suspended from opposite portions of the connecting member.

Earmuffs have been, and are, a significant factor in the hearing protection market. Their use, as a fraction of the total ear protecting device market, has however been declining despite the fact that the number of earmuff manufacturers has increased. This is, in part, due to the poor long-term comfort of these devices. Users have complained of a moist, hot, uncomfortable condition caused by normal perspiration. Muffs are constructed to conform to a wearer's ears so as to maximize their attenuating characteristics. As a result thereof, they do not allow water vapor (perspiration) to escape.

A cooler, more comfortable, sound attenuating earmuff is provided through the present invention. The present invention provides an earmuff which allows water vapor to escape without materially compromising its noise attenuating properties. The present invention provides a porous muff which allows for moisture transmission, yet one which provides attenuation which compares favorably with similar nonporous muffs. The present invention additionally provides a muff which compensates for rapid changes in pressure which occur on aircraft and submarines. It permits an airflow which in turn allows equilibrium pressure to be attained on each side of the eardrum.

A porous muff which provides essentially full attenuation in comparison to similar nonporous muffs is highly unexpected. An article taken from Volume 15, Number 3 of the Journal of the Acoustical Society of America states the following on page 158:

It was found that any small hole in the septum or insert—even the tiny hole of a No. 80 drill—ruined the acoustic insulation.

A similar finding is found in a Jan. 1955 article taken from the same journal (Volume 27). The article entitled, "Factors Determining the Sound Attenuation Produced by Earphone Sockets," states the following on page 146:

In order to obtain high sound attenuation, the air space between the socket and the eardrum must be isolated from the outside air.

Still similar findings appear in U.S. Pat. No. 3,637,040. U.S. Pat. No. 3,637,040 states the following in column 1, lines 10-14:

When the ports are closed, the ear defender assembly provides maximum attenuation to airborne sounds and noises, but when the ports are opened airborne sounds are permited to reach the wearer's ears in a fairly normal manner.

The presence of a "disc or pad 7 of suitably porous material such as felt or preferably plastic" (U.S. Pat. No. 3,637,040) is insignificant. The same is true for the porous or open materials of U.S. Pat. Nos. 1,909,856; 3,454,962; 3,588,914; 3,644,939; 3,661,225; 3,728,741; 3,823,713; 4,094,303; and 4,174,155. None of these patents disclose an earmuff which allows water vapor to escape without materially compromising its noise attenuating properties. None of these patents disclose an earmuff which allows for moisture transmission, yet one which provides attenuation which compares favorably with similar nonporous muffs.

It is accordingly an object of the subject invention to provide a more comfortable ear protecting device for protecting a wearer from disturbing noise levels.

The foregoing and other objects of the invention will become apparent from the following detailed description taken in connection with the accompanying drawings which form a part of this specification, and in which:

FIG. 1 is a perspective view of the structure for a typical hearing protector device within the present invention;

FIG. 2 is a log-log plot of attenuation versus specific airflow resistance at 125 Hz;

FIG. 3 is a log-log plot of attenuation versus specific airflow resistance at 250 Hz;

Figure 4:
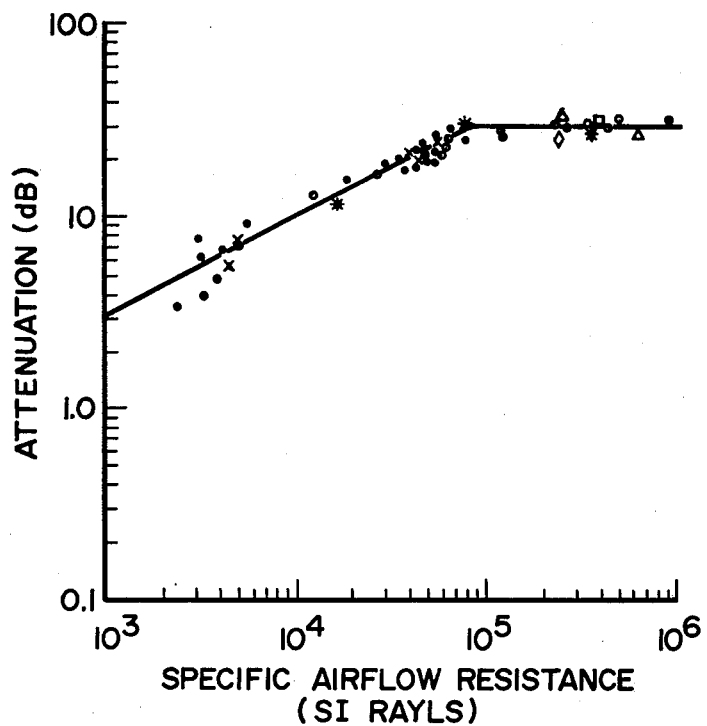
FIG. 4 is a log-log plot of attenuation versus specific airflow resistance at 500 Hz.

The present invention provides an ear protecting device for protecting a wearer from annoying and/or damaging noise levels. The device is comprised of a connecting member and a pair of muffs suitable for covering a wearer's ears. The muffs are suspended from opposite portions of the connecting member. The connecting member can be a band, such as a headband or a helmet with auxiliary hardware or any other means which are, or which may become, known to those skilled in the art. The muffs are permeable to water vapor. Each of the the muffs is at least partially porous. Each of the muffs have a specific airflow resistance of at least 15,000 SI rayls. Each of the muffs have a permeance of at least 2 metric perms.

The desirable combination of properties attributable to the muff of the present invention is achieved by carefully controlling the size, shape and number of pores so as to obtain a specific airflow resistance of at least 15,000 SI rayls on the one hand and a permeance of at least 2 metric perms on the other. Attenuation increases as the specific airflow resistance increases. Water transmission increases as the permeance increases. The specific airflow resistance is usually at least 30,000 SI rayls and preferably at least 60,000 SI rayls. The permeance is usually at least 4 metric perms and preferably at least 6 metric perms.

The mean pore size of the porous portion of the muff is generally no greater than 70 micrometers. Attenuation will decrease with increasing pore size, in those situations wherein the relative pore area and volume remains the same as does the pore length and shape. A mean pore size of no greater than 50 micrometers is usually the case. The mean pore size is preferably less than 20 micrometers.

The structure for a typical hearing protector device within the present invention is shown in FIG. 1. It is comprised of headband 1 and muffs 2. Muffs 2 are comprised of cups 3 and earseal cushions 5. The porous portion of the muff can be either the cup or the earseal cushion or both. The cup and/or the earseal cushion can be partially or entirely porous. The cup can be an entirely porous cup with a coated nonporous portion, a porous cup which has been precompressed to alter its porosity or a nonporous cup with a porous insert. Porosity can be attained using any process and/or material which will provide the specific airflow resistance and permeance of the subject invention. The porous portion of the muff is generally at least 4 square centimeters and preferably at least 6 square centimeters. The porous material can, as stated hereinabove, be any one of a number of materials, which include ultra high molecular weight polyethylene resins, polypropylene, glass frits, ceramics and metals. Ultra high molecular weight polyethylene resins are presently preferred. They typically have a weight average molecular weight of at least $3.5 \times 10^6$ as measured by the solution viscosity method.

Permeance will generally increase with increasing surface area for the porous portion of the muff. The permeance of a totally porous earseal cushion will generally be at least 10 metric perms, and will preferably be at least 12 metric perms. The permeance of a totally porous cup will generally be at least 20 metric perms, and will preferably be at least 40 metric perms. Higher permeances of at least 20, and preferably at least 40, metric perms can also be found in partially porous muffs. An earseal cushion can be totally porous even if it has a nonporous backplate or connecting hardware.

The following examples are illustrative of several aspects of the invention.

EXAMPLE I

Thirty-six porous cups were compression molded from an ultra high molecular weight polyethylene resin. The cups were fabricated with four differing pore sizes, three different wall thicknesses and three different volumes. The cups were subsequently fitted with vinyl covered foam cushions, acoustical foam inserts and a headband.

Each of the cups were tested for attenuation at varying frequencies of from 125 Hz to 8,000 Hz and for specific airflow resistance. Attenuation was determined in accordance with the ANSI-S3.19 blockhead attenuation test using silicone flesh. Specific airflow resistance was determined in accordance with the procedures set forth in ASTM C-522-80. The results of the tests appear hereinbelow in Table I.

TABLE I

PHYSICAL PROPERTIES OF PORUS MUFF CUPS

| Cup No. | Nominal Mean Pore Size (μm) | Wall Thickness (inches) | Cup[1] Wt. (g) | Cup[1] Volume (ml) | Blockhead Attenuation (dB) Hz 125 | 250 | 500 | 1000 | 2000 | 3000 | 4000 | 6000 | 8000 | Specific Airflow Resistance (SI Rayls) |
|---|---|---|---|---|---|---|---|---|---|---|---|---|---|---|
| 1 | 5 | ⅛ | 45 | 103 | 4.5 | 8.0 | 18.5 | 27.0 | 34.0 | 34.0 | 36.0 | 34.0 | 37.0 | $3.61 \times 10^4$ |
| 2 | 5 | ¼ | 59 | 103 | 6.5 | 11.0 | 22.0 | 32.0 | 42.0 | 43.0 | 42.5 | 40.0 | 47.0 | $5.42 \times 10^4$ |
| 3 | 5 | ⅜ | 89 | 103 | 5.0 | 17.0 | 28.5 | 45.1 | 47.0 | 46.0 | 48.0 | 40.0 | 45.0 | $7.5 \times 10^4$ |
| 4 | 5 | ⅛ | 61 | 195 | 8.5 | 16.0 | 25.0 | 31.0 | 36.5 | 34.5 | 31.5 | 35.5 | 37.5 | $5.24 \times 10^4$ |
| 5 | 5 | ¼ | 82 | 195 | 5.5 | 15.0 | 22.5 | 30.0 | 36.0 | 30.5 | 35.5 | 40.5 | 41.5 | $4.39 \times 10^4$ |
| 6 | 5 | ⅜ | 124 | 195 | 10.5 | 23.0 | 33.0 | 47.0 | 38.0 | 35.0 | 39.0 | 41.0 | 42.0 | $7.03 \times 10^4$ |
| 7 | 5 | ⅛ | 71 | 286 | 8.0 | 14.0 | 21.0 | 24.5 | 31.0 | 26.5 | 28.0 | 36.0 | 37.5 | $2.97 \times 10^4$ |
| 8 | 5 | ¼ | 108 | 286 | 10.0 | 21.0 | 29.0 | 33.5 | 36.5 | 34.5 | 32.0 | 41.5 | 45.0 | $5.94 \times 10^4$ |
| 9 | 5 | ⅜ | 158 | 286 | 14.5 | 24.0 | 33.0 | 43.0 | 40.5 | 36.0 | 34.5 | 39.5 | 43.0 | $6.11 \times 10^4$ |
| 10 | 10 | ⅛ | 46 | 103 | 6.5 | 9.0 | 20.0 | 28.0 | 35.5 | 35.5 | 36.0 | 36.0 | 38.0 | $4.15 \times 10^4$ |
| 11 | 10 | ¼ | 60 | 103 | 6.0 | 11.0 | 22.0 | 34.0 | 42.5 | 43.5 | 43.5 | 39.0 | 45.5 | $4.72 \times 10^4$ |
| 12 | 10 | ⅜ | 88 | 103 | 6.0 | 16.0 | 26.0 | 37.5 | 47.0 | 45.0 | 46.0 | 41.0 | 49.0 | $5.49 \times 10^4$ |
| 13 | 10 | ⅛ | 48 | 195 | 6.0 | 13.0 | 21.5 | 27.0 | 32.5 | 30.0 | 30.0 | 34.5 | 36.0 | $3.40 \times 10^4$ |
| 14 | 10 | ¼ | 83 | 195 | 7.0 | 16.0 | 24.0 | 32.0 | 38.0 | 33.0 | 36.5 | 43.0 | 45.5 | $3.89 \times 10^4$ |
| 15 | 10 | ⅜ | 126 | 195 | 9.0 | 19.0 | 27.0 | 39.5 | 36.5 | 34.5 | 40.0 | 43.0 | 45.0 | $4.42 \times 10^4$ |
| 16 | 10 | ⅛ | 70 | 286 | 5.0 | 10.0 | 16.5 | 21.0 | 26.0 | 25.0 | 24.0 | 29.0 | 30.0 | $1.76 \times 10^4$ |
| 17 | 10 | ¼ | 111 | 286 | 9.0 | 19.5 | 25.5 | 31.0 | 36.0 | 35.5 | 32.0 | 41.5 | 44.0 | $4.72 \times 10^4$ |
| 18 | 10 | ⅜ | 156 | 286 | 12.5 | 20.5 | 30.0 | 41.0 | 38.5 | 37.0 | 36.0 | 40.0 | 45.0 | $5.21 \times 10^4$ |
| 19 | 70 | ⅛ | 44 | 103 | 0 | 0.5 | 4.0 | 9.0 | 16.5 | 15.5 | 14.5 | 17.0 | 17.0 | $3.31 \times 10^3$ |
| 20 | 70 | ¼ | 53 | 103 | 0 | 1.0 | 5.0 | 11.0 | 18.0 | 18.0 | 17.5 | 20.5 | 20.5 | $3.90 \times 10^3$ |
| 21 | 70 | ⅜ | 77 | 103 | 4.5 | 6.0 | 10.0 | 16.2 | 23.0 | 24.0 | 25.0 | 28.0 | 28.0 | $5.16 \times 10^3$ |
| 22 | 70 | ⅛ | 61 | 195 | 4.0 | 5.0 | 8.0 | 12.0 | 18.0 | 19.0 | 19.5 | 21.5 | 21.0 | $3.01 \times 10^3$ |
| 23 | 70 | ¼ | 74 | 195 | 0 | 2.0 | 6.0 | 12.0 | 18.0 | 17.5 | 19.0 | 20.0 | 21.0 | $4.23 \times 10^3$ |
| 24 | 70 | ⅜ | 106 | 195 | 0 | 3.0 | 7.0 | 12.5 | 17.5 | 18.0 | 20.5 | 23.0 | 25.0 | $4.13 \times 10^3$ |
| 25 | 70 | ⅛ | 64 | 286 | 1.0 | 1.0 | 3.5 | 8.0 | 12.0 | 14.0 | 14.5 | 14.0 | 14.5 | $2.38 \times 10^3$ |
| 26 | 70 | ¼ | 94 | 286 | 2.0 | 3.5 | 6.5 | 11.0 | 16.0 | 19.5 | 19.5 | 22.0 | 22.0 | $3.00 \times 10^3$ |
| 27 | 70 | ⅜ | 137 | 286 | 1.0 | 3.5 | 7.5 | 13.0 | 16.5 | 20.5 | 22.5 | 23.0 | 24.5 | $4.58 \times 10^3$ |
| 28 | 200 | ⅛ | 43 | 103 | 0 | −1.0 | −1.0 | −3.5 | +2.0 | +5.5 | 5.0 | 9.0 | 9.5 | $1.01 \times 10^2$ |
| 29 | 200 | ¼ | 59 | 103 | 0 | −0.5 | −1.0 | −4.0 | +4.5 | 7.5 | 7.5 | 10.0 | 10.5 | $2.21 \times 10^2$ |
| 30 | 200 | ⅜ | 87 | 103 | −0.5 | −0.5 | −1.5 | −3.0 | +7.0 | 8.5 | 8.0 | 10.0 | 9.5 | $3.12 \times 10^2$ |
| 31 | 200 | ⅛ | 58 | 195 | 0 | 0 | −1.0 | −3.0 | 2.0 | 4.0 | 4.5 | 9.0 | 10.0 | $1.17 \times 10^2$ |
| 32 | 200 | ¼ | 81 | 195 | −0.5 | −1.0 | −1.0 | −4.0 | 4.0 | 5.5 | 8.0 | 10.0 | 10.5 | $1.30 \times 10^2$ |
| 33 | 200 | ⅜ | 123 | 195 | −0.5 | −0.5 | −2.0 | −3.0 | 6.5 | 7.0 | 9.0 | 10.0 | 9.5 | $2.59 \times 10^2$ |
| 34 | 200 | ⅛ | 68 | 286 | 0 | −1.0 | −1.0 | −3.0 | 2.0 | 3.5 | 5.0 | 9.0 | 10.0 | $9.30 \times 10^1$ |
| 35 | 200 | ¼ | 108 | 286 | 0 | −0.5 | −1.5 | −4.0 | 1.0 | 6.0 | 7.0 | 9.0 | 9.0 | $1.20 \times 10^2$ |
| 36 | 200 | ⅜ | 156 | 286 | −0.5 | −1.0 | −2.0 | −3.0 | 5.5 | 8.5 | 9.5 | 10.5 | 11.0 | $2.16 \times 10^2$ |

[1]Cup, cushion back plate, cushion & acoustical foam

Table I clearly shows, contrary to prior beliefs, that porous muffs can have good noise attenuating properties. Table I shows that porous muffs can have good noise attenuating properties if the size, shape and number of pores is controlled as taught herein. The attenuation for Cup Nos. 1-18 is far superior to that for Cup Nos. 19-36. The lowest specific airflow resistance for any of Cup Nos. 1-18 is 17,600 SI rayls. The highest specific airflow resistance for any of Cup Nos. 19-36 is 5,160 SI rayls. The present invention calls for a specific airflow resistance of at least 15,000 SI rayls.

Table I also shows how the size, shape and number of pores affect specific airflow resistance. Specific airflow resistance is shown to decrease with increasing pore size, with decreasing pore length and with an increasing number of pores.

EXAMPLE II

Four commercial nonporous muffs (Muff Nos. A–D) were tested for attenuation at varying frequencies of from 125 Hz to 8,000 Hz. Attenuation was determined in accordance with the ANSI-S3.19 blockhead attenuation test using silicone flesh. The results of the tests appear hereinbelow in Table II, along with those for Cup Nos. 6 and 9 (Example I).

TABLE II

Comparison of ANSI-S3.19 Blockhead Attenuation Data for Commerical Muffs and Porous Muffs

| Muff | Attenuation (dB) ||||||||| Log Average of Nine Frequencies |
|---|---|---|---|---|---|---|---|---|---|---|
|  | 125 | 250 | 500 | 1000 | 2000 | 3000 | 4000 | 6000 | 8000 |  |
| A. | 1 | 18 | 30 | 34 | 45 | 45 | 47 | 43 | 50 | 21 |
| B. | 8 | 20 | 27 | 38 | 46 | 47 | 46 | 43 | 42 | 27 |
| C. | 9 | 18 | 30 | 43 | 41 | 34 | 33 | 34 | 37 | 27 |
| D. | 21 | 24 | 33 | 42 | 50 | 43 | 42 | 43 | 44 | 34 |
| 6. | 11 | 23 | 33 | 47 | 38 | 35 | 39 | 41 | 42 | 30 |
| 9. | 15 | 24 | 33 | 43 | 40 | 36 | 35 | 40 | 43 | 32 |

Table II shows that the average attenuation of the porous muffs is within the range of the solid muffs. The porous muffs of the present invention compare very favorably with the nonporous muffs.

EXAMPLE III

Figure 5:
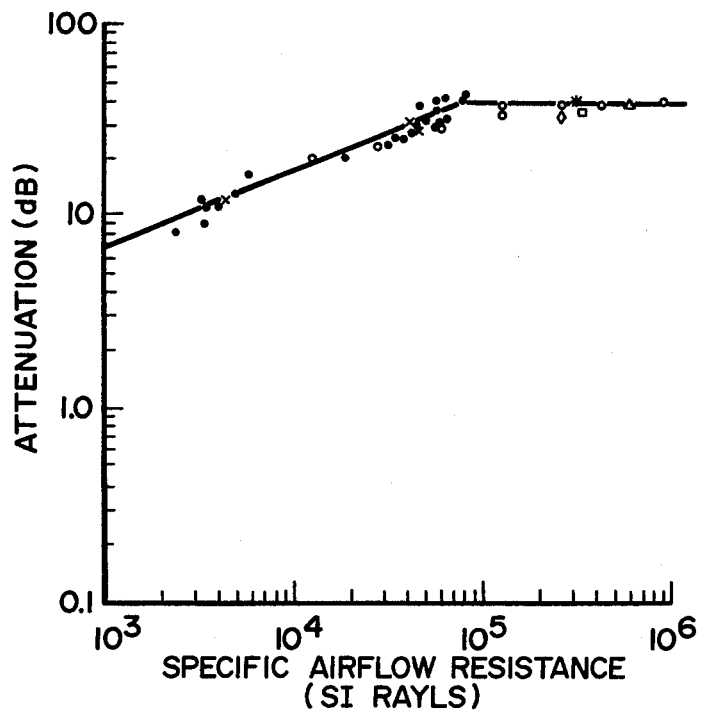
FIG. 5 is log-log plot of attenuation versus specific airflow resistance at 1000 Hz.

A graphical correlation of attenuation versus specific airflow resistance is seen in FIGS. 2–5. FIGS. 2–5 are respectively at 125, 250, 500 and 1000 Hz. Attenuation at 500 and 1000 Hz is more meaningful with respect to hearing protection than is attenuation at the lower frequencies of 125 and 250 Hz. Attenuation was determined in accordance with the ANSI-S3.19 blockhead attenuation test using silicone flesh. Specific airflow resistance was determined in accordance with the procedures set forth in ASTM C-522-80 with the internal area of the cup being used for all calculations regardless of whether the cup was totally or partially porous. The data points are identified as follows:

1. "×"-those cups from Table I having a wall thickness of ¼ inch and a volume of 195 ml.;
2. "●"-the remaining cups from Table I;
3. " ⊙ "-the coated and uncoated cups from Table III hereinbelow;
4. "*"-the cups from Table IV hereinbelow having ultra high molecular weight polyethylene or polypropylene inserts;
5. "△"-the cups from Table IV hereinbelow having ceramic inserts;
6. "□"-the cups from Table IV hereinbelow having glass inserts; and
7. "□"-the cups from Table IV hereinbelow having stainless steel inserts.

FIGS. 2–5 show how attenuation increases with specific airflow resistance. Each of the Figures show a positively sloping line up to a maximum value of 75,000 to 85,000 SI rayls. Both the slopes and intercepts of the lines change with changes in frequency. At values greater than 75,000 to 85,000 SI rayls, the attenuation of the cups are mass-spring controlled. Cups with higher volumes would be above the level line while cups with lower volumes would be below the line.

The data for Table III was obtained by coating Table I cups having a wall thickness of ¼ inch and a volume of 195 ml. The cups had a nominal pore size of either 5, 70 or 200 micrometers. The coating was a thin, light weight, nonporous styrene/unsaturated polyester film. A fully coated muff had a coating weight of from 1 to 2 grams.

TABLE III

ANSI S-3.19 BLOCKHEAD ATTENUATION VALUES AND AIRFLOW RESISTANCE OF PARTIALLY COATED POROUS MUFF CUPS

| Nominal Pore Diameter (μm) | % of Internal Area Coated | Attenuation dB (at Hz) |  |  |  | Specific Airflow Resistance (SI Rayls)* | Coating Method For the Cup |
|---|---|---|---|---|---|---|---|
|  |  | 125 | 250 | 500 | 1000 |  |  |
| 200 | 0 | 6 | 5 | 5 | 3 | $1.62 \times 10^2$ | From Bottom, Up |
| 200 | 50 | 3 | 2 | 1 | 1 | $3.22 \times 10^2$ |  |
| 200 | 75 | 0 | −1 | −4 | 5 | $6.66 \times 10^2$ |  |
| 200 | 88 | 0 | −1 | −4 | 9 | $9.82 \times 10^2$ |  |
| 200 | 94 | 0 | 0 | 7 | 18 | $3.08 \times 10^3$ |  |
| 200 | 100 | 9 | 23 | 34 | 45 | $>1.2 \times 10^7$ |  |
| 70 | 0 | 2 | 8 | 8 | 14 | $4.79 \times 10^3$ | From Bottom, Up |
| 70 | 50 | 3 | 8 | 4 | 20 | $2.60 \times 10^4$ |  |
| 70 | 75 | 5 | 13 | 18 | 24 | $2.60 \times 10^4$ |  |
| 70 | 88 | 9 | 17 | 23 | 30 | $5.65 \times 10^4$ |  |
| 70 | 94 | 11 | 21 | 29 | 26 | $1.19 \times 10^5$ |  |
| 70 | 100 | 14 | 25 | 37 | 42 | $>1.2 \times 10^7$ |  |
| 5 | 0 | 9 | 19 | 27 | 37 | $5.63 \times 10^4$ | From Bottom, Up |
| 5 | 50 | 11 | 20 | 30 | 40 | $1.16 \times 10^5$ |  |
| 5 | 75 | 12 | 25 | 34 | 42 | $2.53 \times 10^5$ |  |
| 5 | 88 | 13 | 26 | 35 | 43 | $4.88 \times 10^5$ |  |
| 5 | 94 | 15 | 26 | 38 | 44 | $8.83 \times 10^5$ |  |
| 5 | 100 | 15 | 27 | 39 | 45 | $>1.2 \times 10^7$ |  |
| 5 | 0 | 10 | 18 | 26 | 37 | $5.20 \times 10^4$ | From Top Center, Down |
| 5 | 50 | 12 | 22 | 32 | 40 | $1.15 \times 10^5$ |  |
| 5 | 75 | 12 | 24 | 35 | 40 | $2.26 \times 10^5$ |  |

TABLE III-continued
ANSI S-3.19 BLOCKHEAD ATTENUATION VALUES AND AIRFLOW RESISTANCE OF PARTIALLY COATED POROUS MUFF CUPS

| Nominal Pore Diameter ($\mu$m) | % of Internal Area Coated | Attenuation dB (at Hz) | | | | Specific Airflow Resistance (SI Rayls)* | Coating Method For the Cup |
|---|---|---|---|---|---|---|---|
| | | 125 | 250 | 500 | 1000 | | |
| 5 | 88 | 12 | 25 | 35 | 42 | $3.40 \times 10^5$ | |
| 5 | 94 | 14 | 26 | 38 | 43 | $4.93 \times 10^5$ | |
| 5 | 100 | 14 | 27 | 39 | 44 | $>1.2 \times 10^7$ | |

*Based on total earmuff cup internal surface area.

The data for Table IV was obtained by inserting porous discs into a commercial muff (Muff C-Table II). The diameter and thickness of the inserts and the nominal pore size thereof are set forth in the table.

TABLE IV
ANSI S3.19 BLOCKHEAD ATTENUATION VALUES AND AIRFLOW RESISTANCE OF VARIOUS POROUS MATERIALS

| Insert Material | Nominal Pore Dia. ($\mu$m) | Disk Insert Diameter (mm) | Thickness (mm) | Attenuation dB (at Hz) | | | | | | | | | Specific Airflow Resistance (SI Rayls)* |
|---|---|---|---|---|---|---|---|---|---|---|---|---|---|
| | | | | 125 | 250 | 500 | 1000 | 2000 | 3150 | 4000 | 6300 | 8000 | |
| a | 10 | 25.4 | 3.2 | 14 | 23 | 32 | 41 | 44 | 35 | 39 | 35 | 38 | $2.95 \times 10^5$ |
| a | 20 | 25.4 | 3.2 | 19 | 25 | 34 | 45 | 42 | 40 | 46 | 44 | 49 | $6.95 \times 10^4$ |
| b | 250 | 25.4 | 3.2 | 0 | 14 | 13 | 21 | 29 | 27 | 31 | 22 | 27 | $1.56 \times 10^4$ |
| c | 50 | 30 | 3.2 | 10 | 22 | 30 | 38 | 37 | 31 | 37 | 39 | 43 | $2.3 \times 10^5$ |
| c | 12 | 30 | 3.2 | 2 | 22 | 32 | 35 | 38 | 38 | 43 | 42 | 42 | $9.4 \times 10^6$ |
| c | 5 | 30 | 3.2 | 17 | 23 | 33 | 41 | 40 | 35 | 43 | 42 | 42 | $5.8 \times 10^5$ |
| d | 15 | 25.4 | 3.2 | 17 | 23 | 32 | 42 | 35 | 37 | 40 | 42 | 40 | $5.8 \times 10^5$ |
| e | 20 | 25.4 | 3.2 | 12 | 24 | 33 | 39 | 39 | 35 | 39 | 43 | 42 | $3.3 \times 10^5$ |

*Based on total earmuff cup internal surface area (148 cm$^2$)
a - Ultra High Molecular Weight Polyethylene
b - Polypropylene
c - Glass Frit
d - Ceramic (SiO$_2$) Beads
e - 316 Stainless Steel

EXAMPLE IV

Ten of the thirty-six cups from Table I, and one other (Cup No. 37), were tested for water vapor transport (permeance) in accordance with a somewhat modified ASTM C-355-64 procedure. Cup No. 37 was compression molded from an ultra high molecular weight polyethylene resin as were the other cups from Table I. The cup parameters and permeance are shown hereinbelow in Table V. The ASTM procedure was modified because of the shape of the cup. Magnesium perchlorate was placed within the cups. A solid domed shaped closure was clamped to the cups. The magnesium perchlorate was rotated between weight readings. The cups were in a room controlled to 60% relative humidity.

TABLE V
WATER VAPOR PERMEANCE OF VARIOUS EARMUFF CUPS

| Cup No. | Nominal Pore Size ($\mu$m) | Cup Area (cm$^2$) External | Internal | Cup Thickness (In.) | Permeance (Metric Perms) |
|---|---|---|---|---|---|
| 37 | 2 | 240 | 182 | .375 | 41.34 |
| 1 | 5 | 82 | 68 | .125 | 88.76 |
| 4 | 5 | 139 | 125 | .125 | 73.67 |
| 6 | 5 | 181 | 125 | .375 | 44.52 |
| 9 | 5 | 240 | 182 | .375 | 44.10 |
| 14 | 10 | 160 | 125 | .250 | 61.42 |
| 20 | 70 | 160 | 125 | .250 | 83.08 |
| 28 | 200 | 82 | 68 | .125 | 67.10 |
| 31 | 200 | 139 | 125 | .125 | 80.35 |
| 33 | 200 | 181 | 125 | .375 | 41.59 |
| 36 | 200 | 240 | 182 | .375 | 41.77 |

Table V clearly shows that cups of the subject invention (Cup Nos. 37, 1, 4, 6, 9 and 14) do permit water vapor transport therethrough. Each of these cups have a permeance in excess of 20 metric perms. This is consistent with the teachings of the present invention which call for a permeance of at least 20 metric perms when the cup is entirely porous.

EXAMPLE V

A test was conducted to determine what percentage of water evaporated from an open container would be transported through cups of the subject invention under the same conditions. The test was conducted at an average temperature of 73° F. and at an average relative humidity of 39%. The surface area of the water was 2.41 cm$^2$. The distance between the surface of the water and the mouth of the cup was 1.524 cm. The results of the test appear hereinbelow in Table VI.

TABLE VI
WATER VAPOR TRANSMISSION OF POROUS MUFF CUPS

| Cup | Internal Surface Area (cm$^2$) | External Surface Area (cm$^2$) | Thickness (cm) | Wt. loss of water in dish after 24 hr | Wt. of water retained by cup | *Percentage of control |
|---|---|---|---|---|---|---|
| Control | — | — | — | 2.7305 g | — | 100.00% |
| Cup 15 Table I | 125.1 | 155 | .9525 | 1.5262 g | .0093 g | 55.55% |
| Cup 16 Table I | 182 | 241 | .3175 | 1.8132 g | .0122 g | 65.96% |

*Corrected for the water retained in the muff cup

Table VI clearly shows that cups of the subject invention do permit a significant amount of water vapor transport therethrough. Cup Nos. 15 and 16 respectively show a water vapor transport of 55.55 and 65.96% of the control (the open container).

EXAMPLE VI

Two muffs were formed by fitting two nonporous cups (Cups E and F) with porous earseal cushions. The cushions were formed by covering foam with selected chamois. The muffs were mounted on a silicone rubber mounting plate (Shore A durometer 20) with enough force to compress the cushions to two-thirds of their original height. The cushion dimensions are shown hereinbelow in Table VII.

TABLE VII

| | Cushion Dimensions | |
|---|---|---|
| Muff | Height (in.) | Internal Perimeter (in.) | External Perimeter (in.) |
| E. | 0.365 | 7.125 | 11.312 |
| F. | 0.475 | 6.312 | 10.812 |

The muffs were tested for specific airflow resistance and water vapor transport (permeance). Specific airflow resistance was determined in accordance with ASTM C-522-80. Water vapor transport was determined in accordance with the modified ASTM C-355-64 procedure discussed hereinabove in Example IV. The results of the tests appear hereinbelow in Table VIII.

TABLE VIII

| Muff | Specific Airflow Resistance (SI Rayls) | Permeance (Metric Perms) |
|---|---|---|
| E. | 3.01 × 10$^4$ | 60.49 |
| F. | 5.57 × 10$^4$ | 50.95 |

The results of Table VIII show that the criteria of the subject invention can be achieved with a porous earseal cushion. Muffs E and F have a specific airflow resistance in excess of 15,000 SI rayls and a permeance in excess of 10 metric perms. The present invention calls for a permeance of at least 10 metric perms when the earseal cushion is entirely porous.

It will be apparent to those skilled in the art that the novel principles of the invention disclosed herein in connection with specific examples thereof will support various other modifications and applications of the same. It is accordingly desired that in construing the breadth of the appended claims they shall not be limited to the specific examples of the invention described herein.

I claim:

1. In an ear protecting device for protecting a wearer from disturbing noise levels, which device is comprised of: a connecting member and a pair of muffs suitable for covering a wearer's ears, said muffs being suspended from opposite portions of the connecting member, said muffs having an inner surface and an outer surface: the improvement comprising; sound attenuating muffs which are permeable to water vapor, each said muff being at least partially porous, pores on said inner surface of each said muff being openly connected with pores on said outer surface of each said muff, each said muff having a specific airflow resistance of at least 30,000 SI rayls, each said muff having a permeance of at least 2 metric perms.

2. An ear protecting device according to claim 1, wherein each said muff has a specific airflow resistance of at least 60,000 SI rayls.

3. An ear protecting device according to claim 1, wherein each said muff has a permeance of at least 4 metric perms.

4. An ear protecting device according to claim 3, wherein each said muff has a permeance of at least 6 metric perms.

5. An ear protecting device according to claim 1, wherein each of said muffs are comprised of a cup and an earseal cushion, each of said cups being at least partially porous.

6. An ear protecting device according to claim 5, wherein each of said cups is entirely porous.

7. An ear protecting device according to claim 1, wherein each of said muffs are comprised of a cup and an earseal cushion, each of said earseal cushions being at least partially porous.

8. An ear protecting device according to claim 7, wherein each of said earseal cushions is entirely porous.

9. An ear protecting device according to claim 1, wherein the mean pore size of the porous portion of the muff is no greater than 70 micrometers.

10. An ear protecting device according to claim 9, wherein the mean pore size of the porous portion of the muff is no greater than 50 micrometers.

11. An ear protecting device according to claim 10, wherein the mean pore size of the porous portion of the muff is no greater than 20 micrometers.

12. An ear protecting device according to claim 5, wherein each of said cups is formed from a porous material and wherein each of said cups has a coated nonporous portion.

13. An ear protecting device according to claim 5, wherein each of said cups is formed from a nonporous material and wherein each of said cups has a porous insert.

14. An ear protecting device according to claim 5, wherein the porous portion of said cup is an ultra high molecular weight polyethylene resin.

15. An ear protecting device according to claim 1, wherein each said muff has a specific airflow resistance of at least 75,000 SI rayls.

16. An ear protecting device according to claim 1, wherein the porous portion of each said muff is at least 4 square centimeters.

17. An ear protecting device according to claim 16, wherein the porous protion of each said muff is at least 6 square centimeters.

18. An ear protecting device according to claim 6, wherein each said muff has a permeance of at least 20 metric perms.

19. An ear protecting device according to claim 18, wherein each said muff has a permeance of at least 40 metric perms.

20. An ear protecting device according to claim 8, wherein each said muff has permeance of at least 10 metric perms.

21. An ear protecting device according to claim 20, wherein each said muff has a permeance of at least 12 metric perms.

22. An ear protecting device according to claim 1, wherein each said muff has a permeance of at least 20 metric perms.

* * * * *